(12) United States Patent
Xia et al.

(10) Patent No.: US 11,180,788 B2
(45) Date of Patent: Nov. 23, 2021

(54) METHOD FOR THE PREPARATION OF LOWER GRAFT DEGREE GLUCOSYLATED STEVIOL GLYCOSIDES

(71) Applicants: Jiangnan University, Wuxi (CN); Dongtai Haorui Biotechnology Co., Ltd., Dongtai (CN)

(72) Inventors: Yongmei Xia, Wuxi (CN); Liping Zhu, Wuxi (CN); Tongtong Zhang, Wuxi (CN); Guoying Du, Dongtai (CN); Xiang Liu, Wuxi (CN); Yun Fang, Wuxi (CN)

(73) Assignees: Jiangnan University, Wuxi (CN); Dongtai Haorui Biotechnology Co., Ltd., Dongtai (CN)

( * ) Notice: Subject to any disclaimer, the term of this patent is extended or adjusted under 35 U.S.C. 154(b) by 0 days.

(21) Appl. No.: 16/525,706

(22) Filed: Jul. 30, 2019

(65) Prior Publication Data

US 2019/0352688 A1    Nov. 21, 2019

Related U.S. Application Data

(63) Continuation of application No. PCT/CN2018/091271, filed on Jun. 14, 2018.

(30) Foreign Application Priority Data

May 31, 2018   (CN) .......................... 201810548972.2

(51) Int. Cl.
*C12P 19/56* (2006.01)
*A23L 27/30* (2016.01)
(Continued)

(52) U.S. Cl.
CPC ............... *C12P 19/56* (2013.01); *A23L 27/36* (2016.08); *C12N 9/2417* (2013.01); *C12N 9/2425* (2013.01); *C12Y 302/01002* (2013.01)

(58) Field of Classification Search
CPC .. A23L 27/36; C12P 19/56; C12Y 302/01002; C12N 9/2425; C12N 9/2417
(Continued)

(56) References Cited

U.S. PATENT DOCUMENTS

2012/0214751 A1 * 8/2012 Markosyan ............. C12P 19/18
514/23
2012/0214752 A1 * 8/2012 Markosyan ............... A23L 2/60
514/23
(Continued)

FOREIGN PATENT DOCUMENTS

CN     102827891 A     12/2012
CN     102925518 A      2/2013
CN     105255971 A      1/2016

*Primary Examiner* — Jennifer M. H. Tichy
(74) *Attorney, Agent, or Firm* — Ipro, PLLC; Na Xu

(57) ABSTRACT

The present invention discloses a method for preparing lower graft degree GSGs, and belongs to the technical field of biosynthesis of sweeteners. The method uses amylase to catalyze hydrolysis of GSGs with a high graft degree, thereby obtaining GSGs with low graft degree mainly containing GSGs with a low grafting number. The content of mono- and di-glucosyl substituents in the SGs in the product was 60% or more of the total glycosides, and the mass percent of the GSGs with a glucosyl grafting number of 3 or less was higher than 70% of the total glycosides. The mono- and di-substituted GSGs obtained by enzyme catalysis by the present invention were structurally similar to those, belong to a mixture of the isomers thereof, and have good sweetness and a flavoring function.

4 Claims, 9 Drawing Sheets

(51) Int. Cl.
*C12N 9/28* (2006.01)
*C12N 9/26* (2006.01)

(58) Field of Classification Search
USPC .................................................. 435/87, 78
See application file for complete search history.

(56) References Cited

U.S. PATENT DOCUMENTS

| | | | | |
|---|---|---|---|---|
| 2013/0287894 A1* | 10/2013 | Markosyan | ............... | A23L 2/54 |
| | | | | 426/48 |
| 2014/0030381 A1* | 1/2014 | Markysyan | ............ | A61K 36/28 |
| | | | | 426/48 |
| 2014/0227394 A1* | 8/2014 | Markosyan | ............ | C12P 19/04 |
| | | | | 426/52 |
| 2014/0227421 A1* | 8/2014 | Markosyan | ............ | C12P 19/18 |
| | | | | 426/551 |
| 2015/0030725 A1* | 1/2015 | Markosyan | ............... | A23L 2/02 |
| | | | | 426/52 |
| 2015/0157045 A1* | 6/2015 | Markosyan | .... | C12Y 302/01001 |
| | | | | 426/48 |

* cited by examiner

METHOD FOR THE PREPARATION OF LOWER GRAFT DEGREE GLUCOSYLATED STEVIOL GLYCOSIDES

TECHNICAL FIELD

The disclosure herein relates to a method for preparation of lower graft degree glucosylated steviol glycosides (GSGs), and belongs to the technical field of biosynthesis of sweeteners.

BACKGROUND

Steviol glycoside (SG) is a general term for up to 64 glycoside molecules in stevia extract, and is composed of a sweet hydrophilic glycosyl group and hydrophobic steviol. Among them, rebaudioside D and rebaudioside M have a good taste, rebaudioside A (RA) has a good taste but a slightly long-lasting sweetness, and stevioside (St), rebaudioside C and other low-molecular weight steviol glycosides (SGs) have a slight bitterness or licorice aftertaste. Such a slightly bitter aftertaste reduces their quality as a natural sweetener. In addition to the bitter taste of impurities affecting the taste quality of a SG product, the steviol molecular structure of the SG itself is also a factor that produces a bitter aftertaste and post-sweetness (i.e., long-lasting sweetness). From the perspective of taste biology, the difference in binding energy between different SGs and sweetness receptors and bitterness receptors is an important factor.

One of the methods for improving the taste of the SGs is to introduce a glycosyl group by enzymatic glycosylation, etc. Due to the steric hindrance of the introduced glycosyl group, the difference in binding energy between the SGs and the sweetness receptors and bitterness receptors is changed, and the taste quality is improved. However, enzymatic glycosylation results in a wide variety of random transglycosylation products, typically glucosyl steviol glycosides (GSGs) with a variety of glucosyl substitution numbers or called grafting numbers, with the grafting number ranging from 1 to 20 in the products. In the GSGs molecules, the total mass percent of low graft number products such as mono- and di-glucosyl grafted SGs is generally less than 50% of the total glycosides, which is so called GSGs with lower graft degree, or lower graft degree GSGs. The sweetness of all GSGs will be reduced to a different extent than the sweetness of the starting material SGs, and the aftertaste, i.e. taste, will also be improved. A product with a high glucosyl substitution number can be used as a flavoring agent and table sugar, but the sweetness is excessively reduced. Products with a low glucosyl substitution number, such as mono- and di-glucosyl substituents of SGs, have good sweetness and a flavoring function, and have a structure same as the isomers of RD and RM with the best taste in natural SGs.

A method for improving the taste of SG by introducing a glycosyl group by an enzymatic glycosylation method or the like is a method for catalyzing trans-glycosides of SG by using cyclodextrin glycosyltransferase from *Bacillus alcalophilus*, and 9 products are obtained. Structural analysis reveals that 1 to 3 glucosyl groups are linked via α-1,4 glycosidic bonds at each of positions C-13 and C-19. When one or two glucosyl groups are linked at the C-13 position, the taste quality is improved compared with St. When three glucosyl groups are linked at the C-13 position, the sweetness is greatly reduced (Fukunaga, 1989). Lobov et al. used pullulanase and Biozyme L for transglycosylation reaction of stevioside to obtain three products respectively. However, the reaction took a long time and the product yield is less than 10% (Lobov, 1991). Abelyan used cyclodextrin as a glycosyl donor to obtain nine transglycosylation products, two of which have better sweetness characteristics but lower yields, and the sum of the yields is 11.6% (Abelyan V A, 2004). Kochikyan used six strains to produce different cyclodextrin glucosyltransferases, and used liquefied starch as a glycosyl donor to catalyze transglycosylation of the stevioside, resulting in seven transglycosylation products (Kochikyan V T, 2006).

Another method for improving the taste of stevioside is to catalyze hydrolysis of starch-modified St by a α-cyclodextrin glucosyltransferase Toruzyme 3.0 L and α-moderate amylase two-enzyme method. After 4 h of reaction, the St conversion rate reached 77.11%, and fourteen stevioside derivatives were obtained. The post-bitter taste of the products was obviously improved, and the taste is sweet. St-Glc 1 and St-Glc 2 with the highest sweetness and the highest yield. With cyclodextrin and stevioside as the substrate, the conversion rate of the stevioside was up to 87.8% after 5 h of reaction when the enzyme amount of the stevioside was 10 U/g (Li W, 2013).

U.S. Pat. Nos. 4,219,571 and 7,807,206 utilized cyclodextrin glucosyltransferases produced by *Bacillus stearothermophilus* to obtain α-1,4 glucosyl derivatives having a degree of polymerization of up to 10.

In the Chinese patent CN105899670 A, a mixture of amylase and cyclodextrin glucosyltransferase was added to a starch suspension, and incubation was carried out at about 75 to 80° C. for about 0.5 to 2 hours. After a liquefied starch suspension formed, the amylase was inactivated by low pH heat treatment. Then steviol glycoside was added to the liquefied starch suspension to form a reaction mixture. A second batch of cyclodextrin glucosyltransferase was added to the reaction mixture, and incubation was carried out at about 5 to 125° C. for about 1 to 168 hours. Subsequently, one or more carbohydrases were added, and the reaction mixture was incubated at about 5 to 125° C. for about 0.0001 to 168 hours. The resulting GSGs composition contains SG derivatives provided about twenty or less α-1,4-glucosyl residues. The resulting product was decolored using the ion exchange resin or membrane. The decolored reaction mixture was absorbed with macroporous resin to remove non-glycosides and then the adsorbed glycosides were eluted with alcohol or aqueous alcohol. The eluent was desalted through a column or membrane filled with ion exchange resin. The alcohol was removed from the eluent to obtain an aqueous eluate. The aqueous eluate was concentrated and dried to obtain dried glucosyl steviosides.

In summary, there is a need to provide a simple production method for obtaining GSGs which mainly have a low grafting number, that is, a product in which the mass content of mono- and di-substituted GSGs exceeds 50%. In such a way, the product sweetness and flavoring function are compromised.

SUMMARY

The present invention aims to provide a simple and economical method for preparation of lower graft degree GSGs in view of the above deficiencies. The mono- and di-glucosyl substituent content of the SGs in the product is 60% or more of the total glycosides, and the mass percent of GSGs with a glucosyl grafting number of 3 or less is higher than 70% of the total glycosides; and the total glycosides refer to GSGs and SGs.

Specifically, hydrolysis of the starting material, that is, the higher graft degree GSGs is catalyzed by an amylase to prepare GSGs with lower graft degree. The product is directly spray dried or slightly concentrated and dried to obtain a crude glucosyl stevioside product. The by-product reducing sugar can be removed by recrystallization, or the by-product reducing sugar or the like can be adsorbed by macroporous resin and then eluted with water, or, removed directly in the process of the macroporous resin absorption section where the GSGs product was processed.

In the starting material GSGs with a high grafting number, the total mass percent of the glucosyl SGs with a grafting number of 4 or more is higher than 40% of the total mass of total glycosides (i.e. all SGs, including GSGs and SGs) (determined by an HPLC method). Or, the total mass percent of the monoglucosyl grafted SGs and the diglucosyl grafted SGs in the higher graft degree GSGs is less than 50% of the total glycosides (determined by the HPLC method). The material is a commercial product well-known to those skilled in the art.

The material higher graft degree GSGs are the product of an enzymatic transglycosylation, and the enzyme is cyclodextrin glycosyltransferase.

The amylase is derived from *Aspergillus niger* sp., *Bacillus licheniformis*, *Bacillus amyloliquefaciens*, *Bacillus subtilis*, *Rhizopus oryzae* or *Aspergillus oryzae*, and is a commercial product in line with GB 2760-2014.

In an example of the present invention, α-amylase derived from *Bacillus subtilis* was used as a catalyst, 60 to 300 g/L higher graft degree GSGs was used as a substrate, and the reaction was carried out at 55 to 60° C. for 3 to 5 h. The amount of the α-amylase can be 1000 to 4000 U/g.

In an example of the present invention, glucoamylase derived from *Aspergillus niger* sp. was used as a catalyst, 60 to 240 g/L higher graft degree GSGs was used as a substrate, and the reaction was carried out at 55 to 60° C. for 3 to 24 h. The substrate concentration is preferably 60 to 240 g/L. The amount of the glucoamylase is preferably 50 to 800 U/g.

In an example of the present invention, α-amylase derived from *Bacillus amyloliquefaciens* was used as a catalyst, 60 to 240 g/L higher graft degree GSGs was used as the substrate, and the reaction was carried out at 55 to 60° C. for 3 to 24 h. The substrate concentration is preferably 60 g/L. The amount of the α-amylase is preferably 50 to 800 U/g.

In an example of the present invention, β-amylase derived from *Bacillus subtilis* was used as a catalyst, 60 to 240 g/L higher graft degree GSGs was used as the substrate, and the reaction was carried out at 55 to 60° C. for 3 to 24 h. The substrate concentration is preferably 60 g/L. The amount of the β-amylase is preferably 50 to 800 U/g.

Beneficial Effects:

The method for preparing lower graft degree GSGs disclosed by the present invention adopts a single enzyme, uses higher graft degree glucosyl SGs as a substrate, has a short reaction time and a simple process, and can obtain lower graft degree glucosyl SGs with high sweetness and good mouthfeel at high throughput.

The most popular SGs currently on the market are RD and RM, i.e., mono- and di-substituted glucosyl products of RA at position C19 respectively. The mono- and di-substituted GSGs obtained by enzyme catalysis by the method are structurally similar to those, belong to a mixture of the isomers of the RD and RM, and have good sweetness and a flavoring function.

BRIEF DESCRIPTION OF FIGURES

FIG. 9A: the concentration of substrate was 100 mg/mL; FIG. 9B: the concentration of substrate was 150 mg/mL; FIG. 9C: the concentration of substrate was 200 mg/mL; Time(h): ■: 1; ●: 3; ♦: 7; X: 11; ▲: 24.

FIG. 10A: preparation of GSG with a low grafting number under pH 5.0; FIG. 10B: preparation of GSG with a low grafting number under pH 6.0; FIG. 10C: preparation of GSG with a low grafting number under pH 6.5; Time(h): □: 0, ■: 1, ●: 3, ♦7; x: 11, ▲: 24.

FIG. 11A: preparation of GSG with a low grafting number by 40 U/g glycoside; FIG. 11B: preparation of GSG with a low grafting number by 300 U/g glycoside; FIG. 11C: preparation of GSG with a low grafting number by 400 U/g glycoside; Time(h): □: 0; ●: 3; X: 12; ▲: 24.

DETAILED DESCRIPTION

Figure 1:
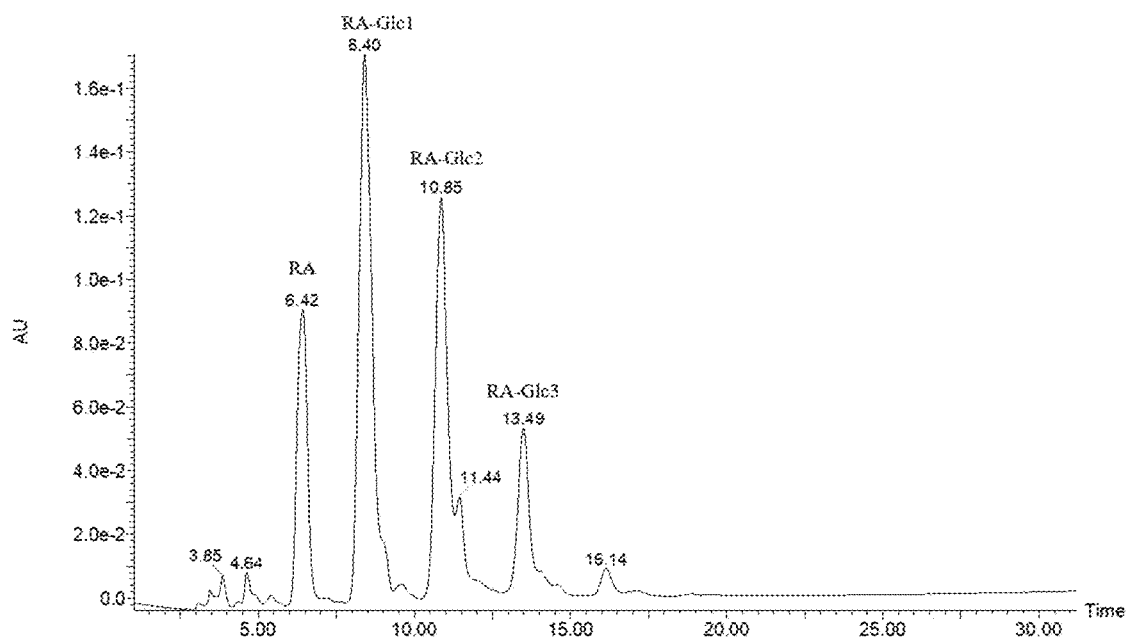
FIG. 1 is the HPLC proof of hydrolysis of GSG catalyzed by *Bacillus subtilis* α-amylase (4000 U/g glycoside).

Analytical Calculation Method:

(1) The qualitative analysis of GSG adopted qualitative determination of a transglycosylation product using liquid chromatography tandem quadrupole time-of-flight mass spectrometer, and the detection conditions were as follow: an ACQUITY UPLC BEH HILIC amino chromatographic column was used, the column temperature was 30° C., gradient elution was carried out under the condition that acetonitrile:water=80:20, (2 min)–50:50 (30 min)(v/v), the injection volume was 1 µL, the injection concentration was 5 mg/mL, and the flow rate was 0.3 mL/min; the mass spectrometry condition: the collision voltage was 6 eV; the ionization mode adopts electrospray ionization (ESI) and a negative ion detection mode were applied, and the molecular weight range detected was 200 to 2000.

(2) The quantitative analysis of GSG was based on an analytical method for determination of GSG in document No. 8 of the GB 2760-2014 Supplementary Document of the National Health Commission.

(3) The glucoamylase activity and α-amylase activity were determined by an enzyme activity measurement method as in GB1886.174-2016.

EXAMPLE 1

Synthesis of Lower Graft Degree GSG Using α-Amylase Derived from *Bacillus Subtilis* as Catalyst Lower graft degree GSG was prepared using GSG derived from rebaudioside A as the starting material. The starting material is a commodity obtained from rebaudioside A and dextrin by transglycosylation catalyzed by a cyclodextrin glucose transferase. The mass percent of rebaudioside A in the starting material is 8.3%, and the total mass percent of mono- and di-substituents (monoglucosyl grafted SGs and diglucosyl grafted stevioside) is 23.3%.

20 g of water was added to a jacketed reactor, and after heating to 60° C., 1.2 g of starting material glycoside was added. After dissolving by stirring, an aqueous solution of α-amylase derived from *Bacillus subtilis* (produced by Wuxi Xuemei Enzyme Company) was added to the jacketed reactor, with a dosage of 4000 U/g of starting material during stirring. The reaction was carried out at 60° C. for 5 h and then the reaction was terminated. The content of total glycosides in the product was 98.7%, and the contents of mono- and di-substituted glucosyl SGs were 36.8% and 34.4% respectively, totally 71.2%. The total content of mono-, di-, and tri-substituted glucosyl SGs was 86.1%, and the sweetness and flavoring function were good. The high pressure liquid chromatography diagram of the product after hydrolysis was shown in FIG. 1 of the specification.

EXAMPLE 2

Synthesis of Lower Graft Degree GSG Using Glucoamylase Derived from *Aspergillus* sp. as Catalyst Lower graft degree GSGs was prepared using glucosyl SGs derived from rebaudioside A as the starting material. The mass percent of rebaudioside A in the starting material was 9.8%, and the total mass percent of mono- and di-substituents was 30.5%.

Figure 2:
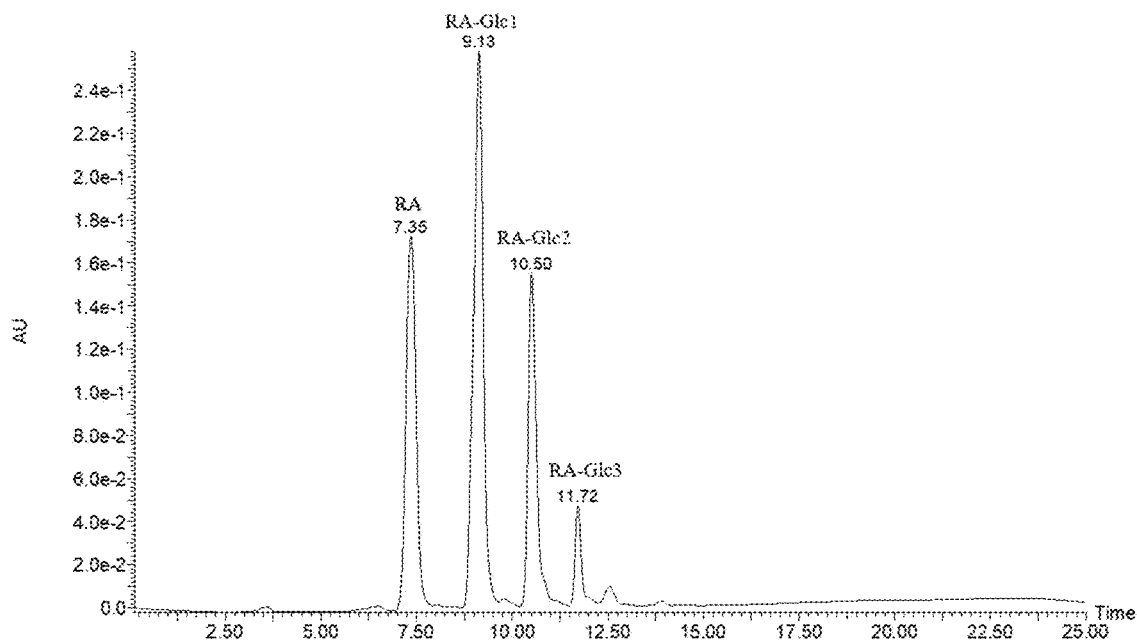
FIG. 2 is the HPLC proof of hydrolysis of GSG catalyzed by *Aspergillus niger* sp. glucoamylase (50 U/g glycoside).

20 g of water was added to a jacketed reactor, and after heating to 55° C., 4.8 g of starting material glycoside was added. After dissolving by stirring, an aqueous solution of glucoamylase derived from *Aspergillus* sp. (produced by Shandong Xiya Chemical Industry Co., Ltd.) was added to the jacketed reactor, with a dosage of 50 U/g of starting material glycoside during stirring. The reaction was carried out at 55° C. for 7.5 h and then the reaction was terminated. The content of total glycosides in the product was 99.4%, and the contents of mono- and di-substituted GSGs were 43.9% and 25.9% respectively, totally 69.8%. The total content of mono-, di-, and tri-substituted GSGs was 76.3%, and the sweetness and flavoring function were good. The high pressure liquid chromatography diagram of the product after hydrolysis was shown in FIG. 2 of the specification.

EXAMPLE 3

Synthesis of Lower Graft Degree GSGs Using Glucoamylase Derived from *Aspergillus* sp. as Catalyst Lower graft degree GSGs was prepared using GSGs derived from rebaudioside A as the starting material. The mass percent of rebaudioside A in the starting material was 9.8%, and the total mass percent of mono- and di-substituents was 30.5%.

Figure 3:
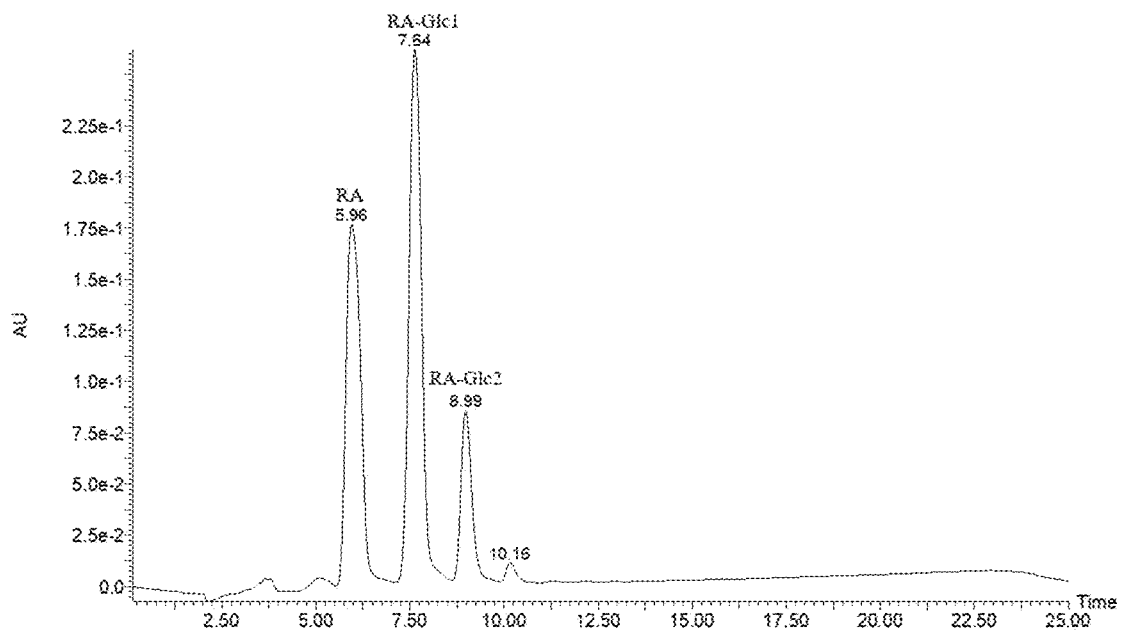
FIG. 3 is the HPLC proof of hydrolysis of GSG catalyzed by *Aspergillus niger* sp. glucoamylase (100 U/g glycoside).

20 g of water was added to a jacketed reactor, and after heating to 55° C., 1.2 g of starting material glycoside was added. After dissolving by stirring, an aqueous solution of glucoamylase derived from *Aspergillus* sp. was added to the jacketed reactor, with a dosage of 100 U/g of starting material glycoside during stirring. The reaction was carried out at 55° C. for 2.5 h and then the reaction was terminated. The content of total glycosides in the product was 98.0%, and the contents of mono- and di-substituted GSGs were 40.2% and 25.3% respectively, totally 65.5%. The total content of mono-, di-, and tri-substituted GSGs was 75.6%, and the sweetness and flavoring function were good. The high pressure liquid chromatography diagram of the product after hydrolysis was shown in FIG. 3 of the specification.

EXAMPLE 4

Synthesis of Lower Graft Degree GSGs Using Glucoamylase Derived from *Aspergillus* sp. as Catalyst Lower graft degree GSGs was prepared using GSGs derived from rebaudioside A as the starting material. The mass percent of rebaudioside A in the starting material was 6.8%, and the total mass percent of mono- and di-substituents was 21.2%.

Figure 4:
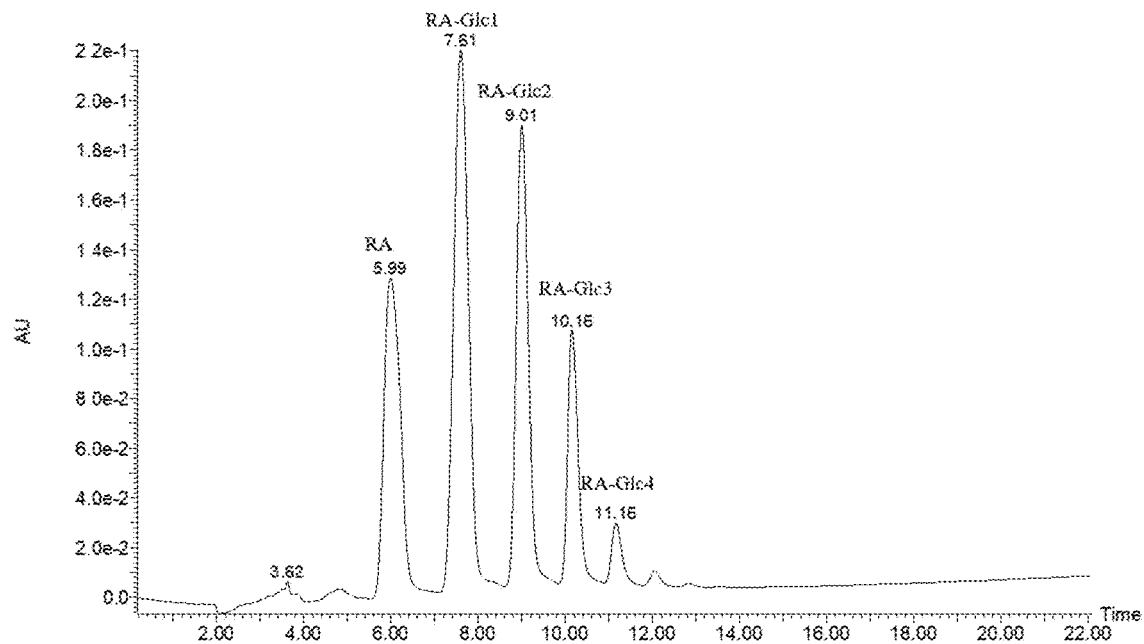
FIG. 4 is the HPLC proof of hydrolysis of GSG catalyzed by *Aspergillus niger* sp. glucoamylase (300 U/g glycoside).

20 g of water was added to a jacketed reactor, and after heating to 55° C., 1.2 g of starting material glycoside was added. After dissolving by stirring, an aqueous solution of glucoamylase derived from *Aspergillus* sp. was added to the jacketed reactor, with a dosage of 300 U/g of starting material glycoside during stirring. The reaction was carried out at 55° C. for 0.5 h and then the reaction was terminated. The content of total glycosides in the product was 99.0%, and the contents of mono- and di-substituted GSGs were 36.5% and 28.9% respectively, totally 65.4%. The total content of mono-, di-, and tri-substituted glucosyl SGs was 80.2%, and the sweetness and flavoring function were good. The high pressure liquid chromatography diagram of the product after hydrolysis was shown in FIG. 4 of the specification.

EXAMPLE 5

Synthesis of Lower Graft Degree GSGs Using α-Amylase Derived from *Bacillus Amyloliquefaciens* as Catalyst Lower graft degree GSGs was prepared using GSGs in which the mass percent of rebaudioside A was 8.3% and the total mass percent of mono- and di-substituents was 23.3% as the starting material.

Figure 5:
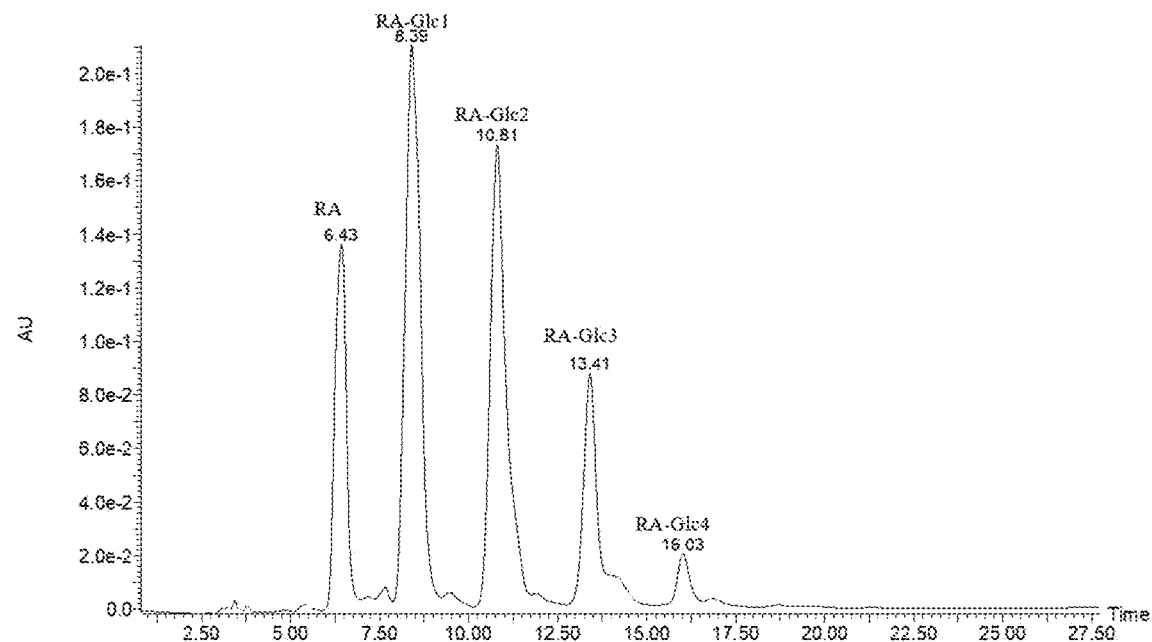
FIG. 5 is the HPLC proof of hydrolysis of GSG catalyzed by *Bacillus amyloliquefaciens* α-amylase (800 U/g glycoside).

20 g of water was added to a jacketed reactor, and after heating to 60° C., 1.2 g of glycoside was added. After dissolving by stirring, an aqueous solution of α-amylase derived from *Bacillus amyloliquefaciens* was added to the jacketed reactor, with a dosage of 800 U/g of starting material glycoside during stirring. The reaction was carried out at 60° C. for 24 h and then the reaction was terminated. The content of total glycosides in the product was 99.0%, and the contents of mono- and di-substituted GSGs were 33.7% and 34.0% respectively, totally 67.7%. The total content of mono-, di-, and tri-substituted GSGs was 85.1%, and the sweetness and flavoring function were good. The high pressure liquid chromatography diagram of the product after hydrolysis was shown in FIG. 5 of the specification.

EXAMPLE 6

Synthesis of Lower Graft Degree GSGs Using β-Amylase Derived from *Bacillus Licheniformis* as Catalyst Lower graft degree GSGs was prepared using GSGs in which the content of rebaudioside A was 9.1% and the total content of mono- and di-substituents was 23.7% as the starting material.

Figure 6:
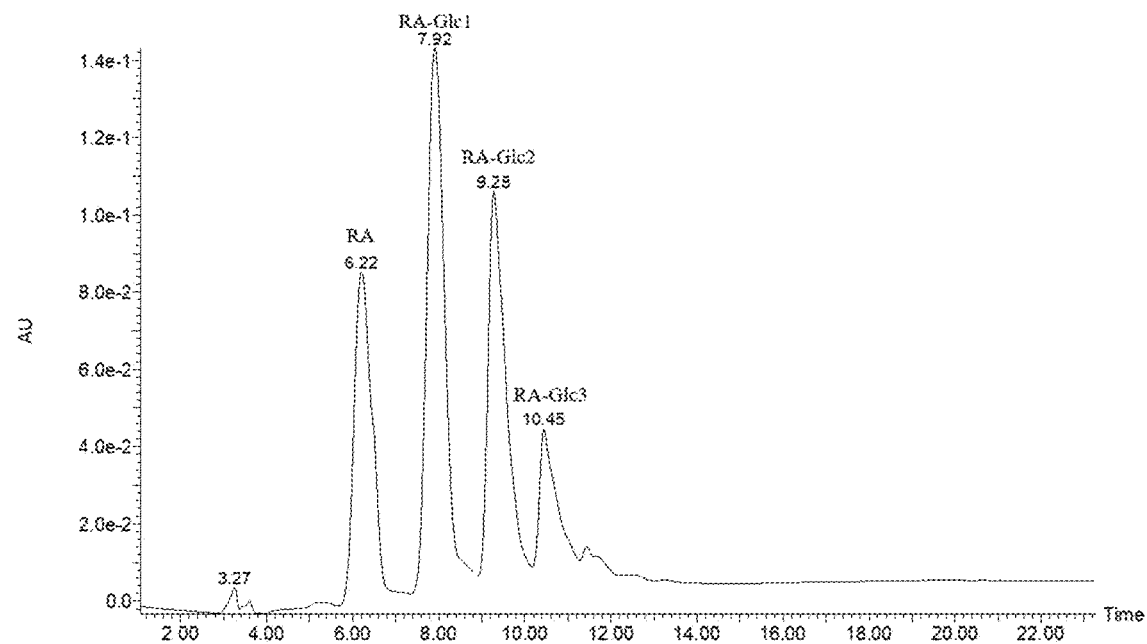
FIG. 6 is the HPLC proof of hydrolysis of GSG catalyzed by *Bacillus licheniformis* β-amylase (300 U/g glycoside).

20 g of water was added to a jacketed reactor, and after heating to 60° C., 4 g of glycoside was added. After dissolving by stirring, an aqueous solution of β-amylase derived from *Bacillus licheniformis* was added to the jacketed reactor, with a dosage of 300 U/g of starting material glycoside during stirring. The reaction was carried out at 60° C. for 3 h and then the reaction was terminated. The content of total glycosides in the product was 92.4%, the contents of mono- and di-substituted GSGs were 33.3% and 27.2% respectively, totally 60.5%, and the sweetness and flavoring function were good. The total content of mono-, di-, and tri-substituted GSGs was 71.7%. The high pressure liquid chromatography diagram of the product after hydrolysis was shown in FIG. 6 of the specification.

EXAMPLE 7

Synthesis of Lower Graft Degree GSGs Using α-Amylase Derived from *Bacillus Licheniformis* as Catalyst Lower graft degree GSGs was prepared using GSGs in which the content of rebaudioside A was 8.3% and the total content of mono- and di-substituents was 23.3% as the starting material.

Figure 7:
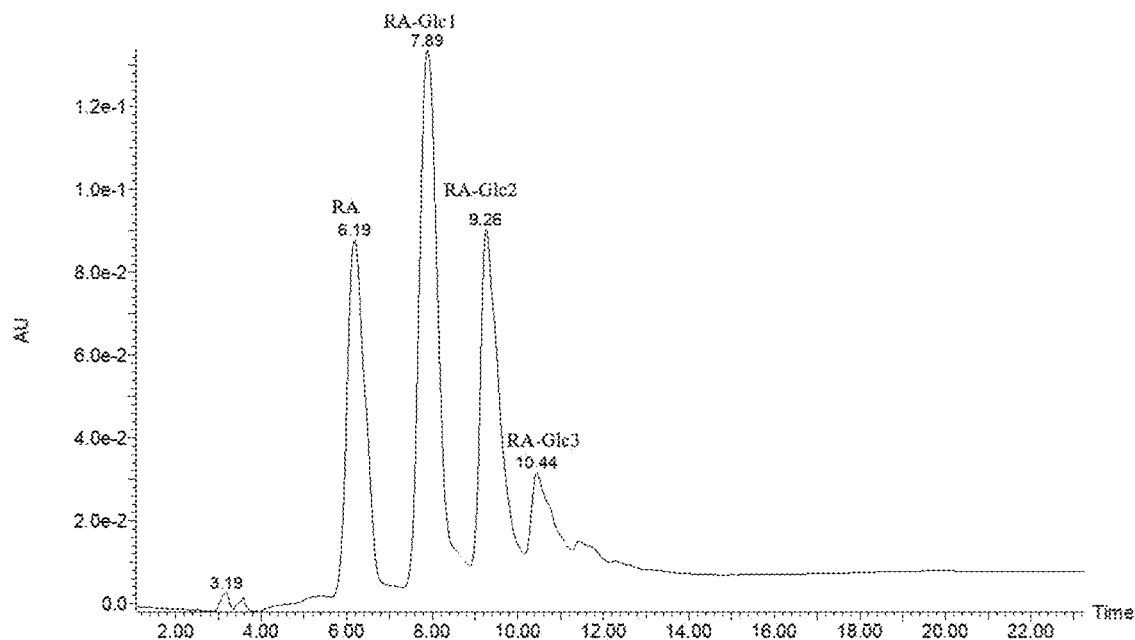
FIG. 7 is the HPLC proof of hydrolysis of GSG catalyzed by *Bacillus licheniformis* α-amylase (300 U/g glycoside).

20 g of water was added to a jacketed reactor, and after heating to 85° C., 6 g of glycoside was added. After dissolving by stirring, an aqueous solution of α-amylase derived from *Bacillus licheniformis* was added to the jacketed reactor, with a dosage of 300 U/g of starting material glycoside during stirring. The reaction was carried out at 85° C. for 3 h and then the reaction was terminated. The content of total glycosides in the product was 95.6%, the contents of mono- and di-substituted GSG were 37.7% and 25.9% respectively, totally 63.6%. The total content of mono-, di-, and tri-substituted GSGs was 71.6%. The high pressure liquid chromatography diagram of the product after hydrolysis was shown in FIG. 7 of the specification.

EXAMPLE 8

Synthesis of Lower Graft Degree GSGs Using Glucoamylase Derived from *Aspergillus* sp. as Catalyst Lower graft degree GSGs was prepared using GSGs in which the content of rebaudioside A was 9.8% and the total content of mono- and di-substituents was 30.5% as the starting material.

Figure 8:
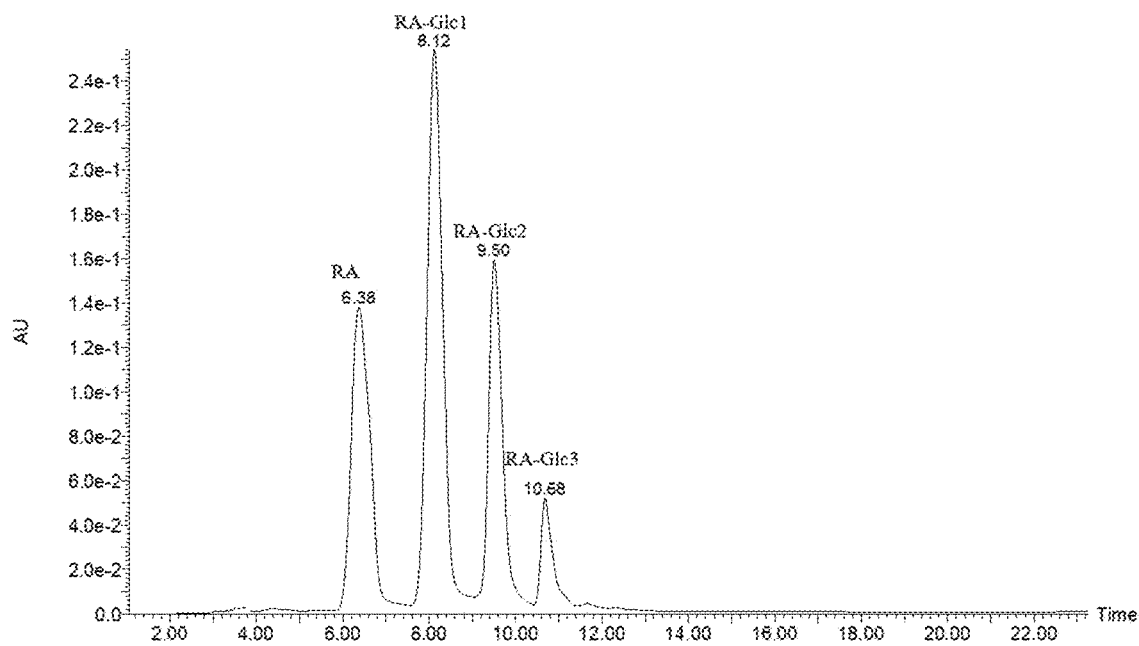
FIG. 8 is the HPLC proof of hydrolysis of GSG catalyzed by *Aspergillus niger* sp. glucoamylase (50 U/g glycoside, 60° C.).

20 g of water was added to a jacketed reactor, and after heating to 60° C., 5 g of glycoside was added. After dissolving by stirring, an aqueous solution of glucoamylase derived from *Aspergillus* sp. was added to the jacketed reactor, with a dosage of 50 U/g of starting material glycoside during stirring. The reaction was carried out at 60° C. for 7 h and then the reaction was terminated. The content of total glycosides in the product was 96.1%, the contents of mono- and di-substituted GSGs were 47.6% and 15.3% respectively, totally 62.9%. The total content of mono-, di-, and tri-substituted GSGs was 71.9%. The high pressure liquid chromatography diagram of the product after hydrolysis was shown in FIG. 8 of the specification.

EXAMPLE 9

Effect of Starting Material Glycoside Concentration on Preparation of Lower Graft Degree GSGs The starting material glycoside was prepared at 60° C. into solutions with the concentration of 100 g/L, 150 g/L and 200 g/L respectively for reaction. An aqueous solution of α-amylase derived from *Bacillus subtilis* was added to the above solutions, with a dosage of 300 U/g of starting material glycoside during stirring. The contents of various SGs in the products were determined after reacting at 60° C. for different times. The results were shown in FIG. 9 of the specification.

Figure 9A:
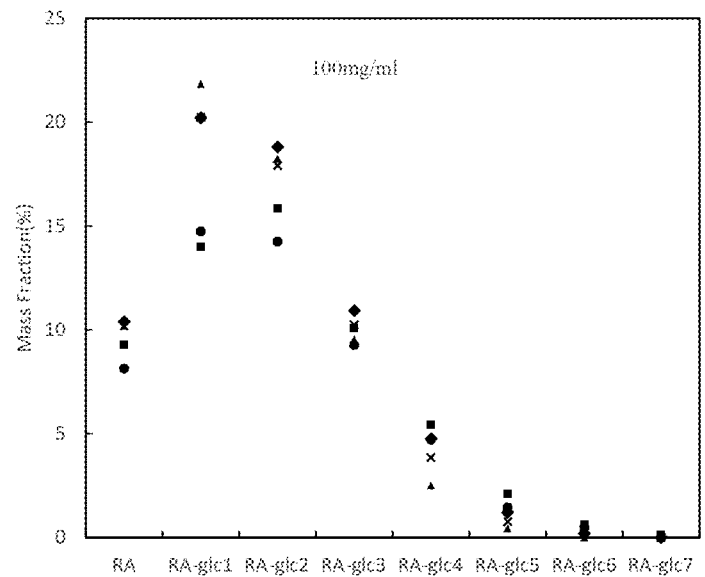
FIG. 9A to 9C each is the effect of substrate concentration on preparation of lower graft degree GSGs.
Figure 9B:
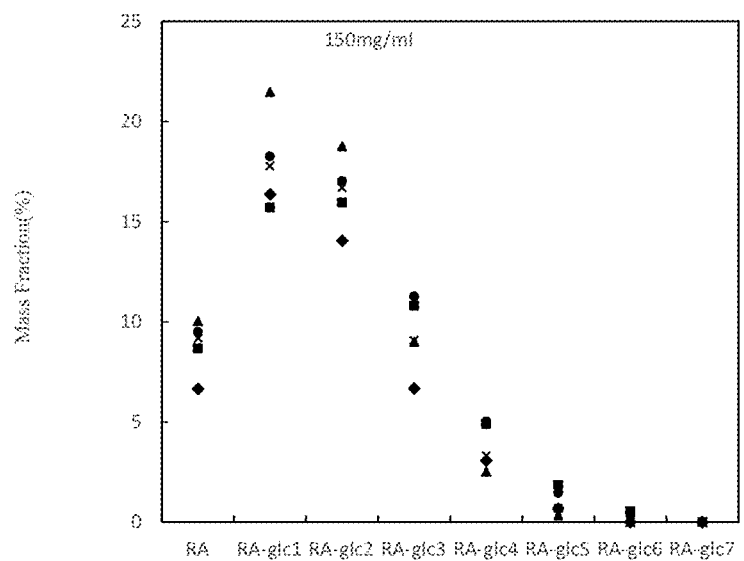
Figure 9C:
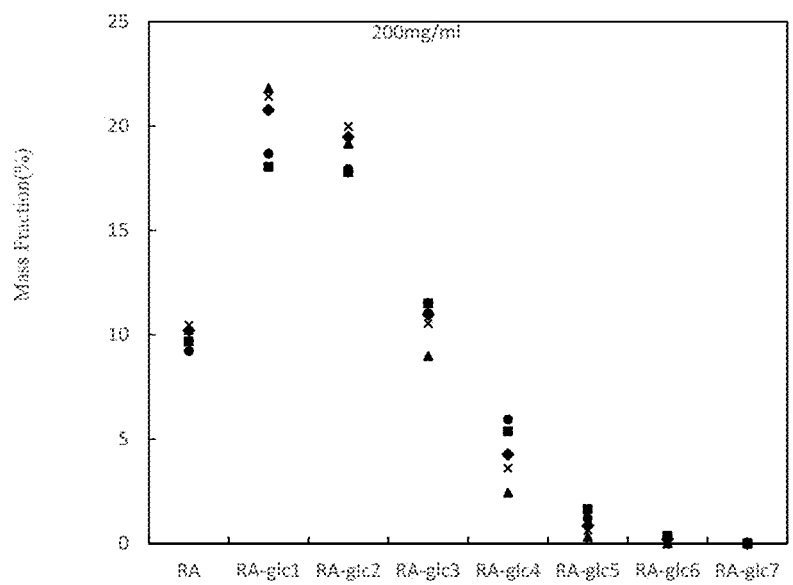

It can be seen from FIG. 9 that the increase in substrate concentration within the scope of experiment has no significant effect on the preparation of the lower graft degree GSGs. Certainly, the degree of influence may vary depending on the type of amylase. As the reaction time prolongs, within a certain range, the concentration of products with a high graft degree rapidly decreases, while the concentration of products with a low graft degree rapidly increases.

EXAMPLE 10

Effect of pH on Preparation of Lower Graft Degree GSGs

Figure 10A:
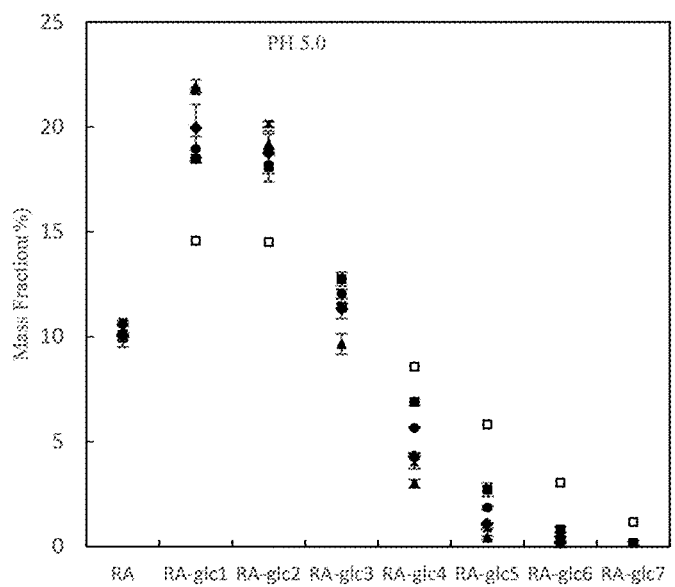
FIG. 10A to 10C each is the effect of pH on preparation of lower graft degree GSGs.
Figure 10B:
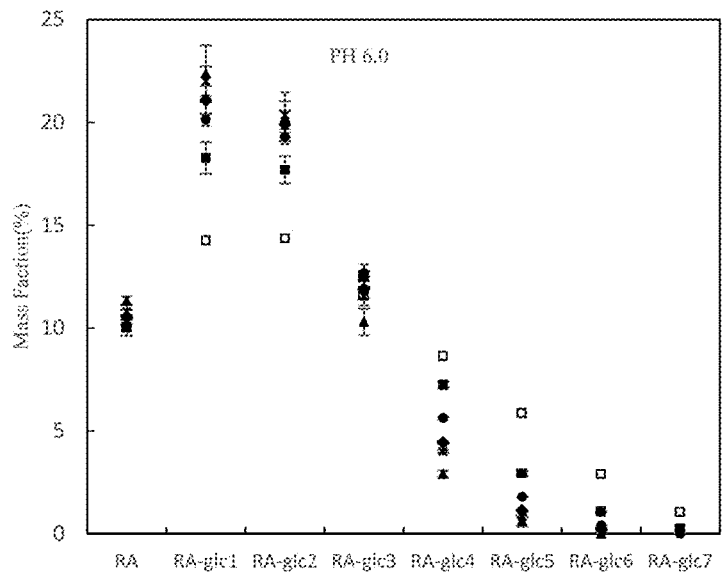
Figure 10C:
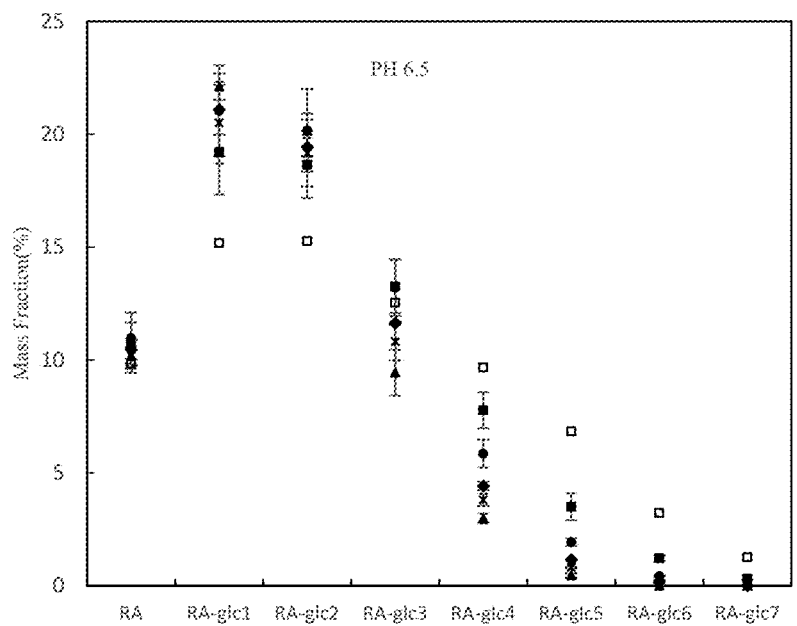

The starting material glycoside was prepared into solutions with a concentration of 100 g/L at 60° C. for reaction with sodium dihydrogen phosphate-disodium hydrogen phosphate buffers (10 mmol/L) with different pH values. An aqueous solution of α-amylase derived from *Bacillus subtilis* was added to the above solutions, with a dosage of 300 U/g of starting material glycoside during stirring. The contents of various SGs in the products were determined after reacting at 60° C. for different times. The results were shown in FIG. 10 of the specification.

EXAMPLE 11

Effect of Enzyme Amount on Preparation of Lower Graft Degree GSGs

Figure 11A:
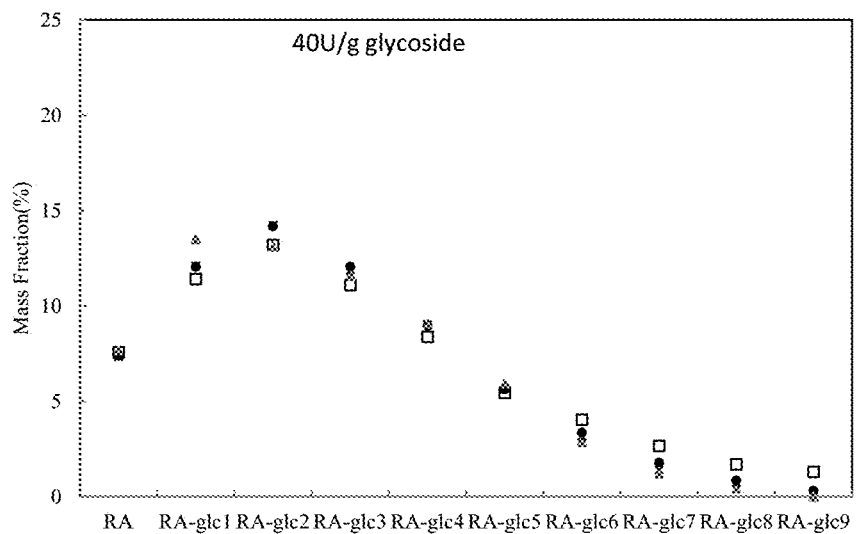
FIG. 11A to 11C each is the effect of the enzyme amount on preparation of lower graft degree GSGs.
Figure 11B:
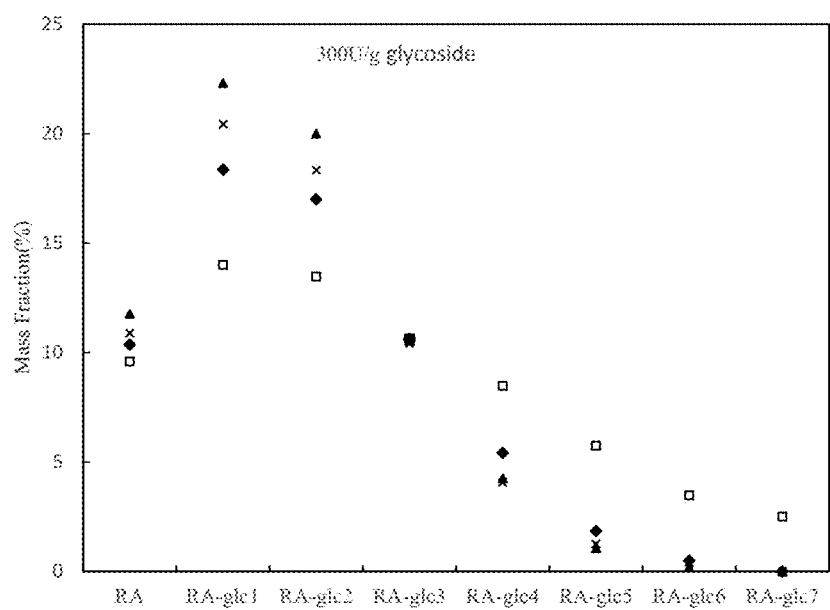
Figure 11C:
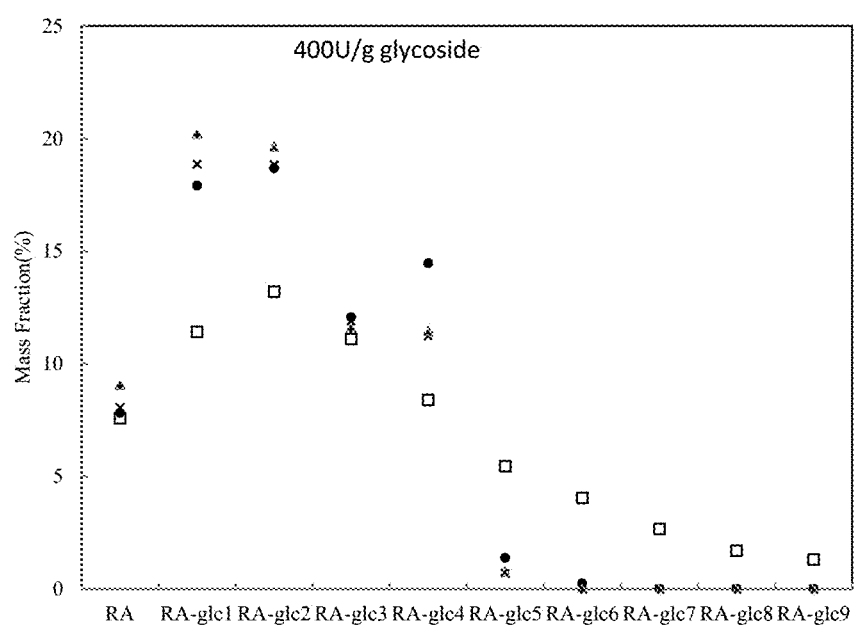

The starting material glycoside was prepared into solutions with a concentration of 100 g/L with water for reaction at 70° C. respectively. An aqueous solution of α-amylase derived from *Bacillus subtilis* was added to the above solutions, with a dosage of 300 U/g of starting material glycoside during stirring. The contents of various SGs in the products were determined after reacting at 70° C. for different times. The results were shown in FIG. 11 of the specification.

What is claimed is:

1. A method for preparing a lower graft degree glucosylated steviol glycosides (GSGs) composition, wherein said method comprises:
   hydrolyzing a starting material composition comprising higher graft degree GSGs at from 55° C. to 60° C. for 3 to 24 hours, wherein hydrolyzing is catalyzed by 1000 to 4000 Units of α-amylase per gram of starting material,
   wherein the lower graft degree GSGs are GSGs with a grafting number of one to three, and the higher graft degree GSGs are GSGs with a grafting number of four or more,
   wherein total glycosides of the lower graft degree GSGs comprises both GSGs and steviol glycosides (SGs),
   wherein the lower graft GSGs comprise 60% or higher of the total glycosides and have a mass percent of more than 85.1% of the total glycosides,
   wherein the α-amylase derived from *Bacillus subtilis*, and wherein the starting material composition comprises 60 g/L to 240 g/L of the higher graft degree GSGs.

2. The method according to claim 1, wherein:
a total mass percent of the higher graft degree GSGs in the starting material composition is higher than 40% of a total mass of total glycosides; or,
a total mass percent of monoglucosyl grafted SGs and diglucosyl grafted SGs in the starting material composition is lower than 50% of the total mass of the total glycosides.

3. The method according to claim 1, further comprising one or more of:
   (a) recrystallizing the crude GSG product; and
   (b) adsorbing a by-product reducing sugar in the lower graft degree GSGs composition, produced by recrystallization of the lower graft degree GSGs composition, by macroporous resin and then eluting with water.

4. The method according to claim 1, wherein hydrolyzing is performed for 3 hours to 5 hours.

\* \* \* \* \*